(12) United States Patent
Kong et al.

(10) Patent No.: US 11,460,451 B2
(45) Date of Patent: Oct. 4, 2022

(54) METHOD FOR SIMULTANEOUSLY DETERMINING FAT-SOLUBLE VITAMINS AND CAROTENOIDS IN SERUM

(71) Applicant: Xi'an Jiaotong University, Xi'an (CN)

(72) Inventors: Liyun Kong, Xi'an (CN); Jiaqi Wang, Xi'an (CN); Yan Liu, Xi'an (CN); Min Wu, Xi'an (CN); Lijuan Shi, Xi'an (CN); Rui Zhang, Xi'an (CN); Menglu Wu, Xi'an (CN); Guoli Li, Xi'an (CN); Feifei Qi, Xi'an (CN); Le Ma, Xi'an (CN)

(73) Assignee: Xi'an Jiaotong University, Xi'an (CN)

( * ) Notice: Subject to any disclaimer, the term of this patent is extended or adjusted under 35 U.S.C. 154(b) by 260 days.

(21) Appl. No.: 17/039,774

(22) Filed: Sep. 30, 2020

(65) Prior Publication Data
US 2021/0190733 A1 Jun. 24, 2021

(30) Foreign Application Priority Data
Dec. 18, 2019 (CN) .......................... 201911311503.X

(51) Int. Cl.
*G01N 30/06* (2006.01)
*G01N 30/74* (2006.01)
(Continued)

(52) U.S. Cl.
CPC ............. *G01N 30/06* (2013.01); *G01N 30/74* (2013.01); *G01N 30/8637* (2013.01);
(Continued)

(58) Field of Classification Search
CPC .. G01N 30/06; G01N 30/74; G01N 2030/027; G01N 2030/062; G01N 33/82;
(Continued)

(56) References Cited

U.S. PATENT DOCUMENTS

2011/0226944 A1* 9/2011 Holmquist ......... G01N 30/7233
250/282

FOREIGN PATENT DOCUMENTS

| CN | 103175934 A | 6/2013 |
|---|---|---|
| CN | 103664725 A | 3/2014 |

(Continued)

OTHER PUBLICATIONS

Rpberta Andreoli, Paola Manini, Diana Poli, Enrico Bergamaschi, Antonio Mutti, Wilfried M. A. Niessen: Development of a implified method for the simultaneous determination of retinol, α-tocopherol, and Ë-carotene in serum by liquid chromatography-tandem mass spectrometry, Published online: Nov. 2003. (Year: 2003).*

(Continued)

*Primary Examiner* — Francis C Gray
(74) *Attorney, Agent, or Firm* — Bookoff McAndrews, PLLC

(57) ABSTRACT

A method for simultaneously determining fat-soluble vitamins and carotenoids in serum, and belonging to the technical field of analytical chemistry, includes an ionic liquid (IL) or a binary mixed solvent composed of an IL and another solvent is adopted as an extractant; the biological samples are pre-treated by liquid-liquid extraction (LLE) and then detected by high-performance liquid chromatography (HPLC); retinyl acetate and trans-β-apo-8'-carotenal are adopted as the internal standards for fat-soluble vitamins and carotenoids, respectively; and the internal standard method is adopted to establish standard curves for quantification based on the retention time and the UV-Vis absorption spectrum. Compared with the existing methods, in the disclosure, the pretreatment process is simple and easy to be conducted, the sample can be prepared in a short time, and the toxic and harmful organic solvent is used at a reduced amount.

7 Claims, 8 Drawing Sheets

(51) Int. Cl.
*G01N 30/86* (2006.01)
*G01N 30/02* (2006.01)
*G01N 30/04* (2006.01)

(52) U.S. Cl.
CPC . *G01N 2030/027* (2013.01); *G01N 2030/045* (2013.01); *G01N 2030/062* (2013.01)

(58) Field of Classification Search
CPC ....... G01N 2030/067; G01N 2030/884; G01N 30/02
See application file for complete search history.

(56) References Cited

FOREIGN PATENT DOCUMENTS

| CN | 104155386 | A |   | 11/2014 |   |
|---|---|---|---|---|---|
| CN | 104749293 | A |   | 7/2015 |   |
| CN | 105158394 | A |   | 12/2015 |   |
| CN | 105372374 | A |   | 3/2016 |   |
| CN | 105717209 | A |   | 6/2016 |   |
| CN | 105891384 | A |   | 8/2016 |   |
| CN | 107561171 | A |   | 1/2018 |   |
| CN | 108008047 | A |   | 5/2018 |   |
| CN | 108120788 | A |   | 6/2018 |   |
| CN | 109030648 | A |   | 12/2018 |   |
| CN | 105891384 | B |   | 3/2019 |   |
| CN | 110174477 | A | * | 8/2019 | ............. G01N 30/02 |
| CN | 110542735 | A | * | 12/2019 |   |
| KR | 10-2018-0047523 | A |   | 5/2018 |   |
| WO | WO 2013/176454 | A1 |   | 11/2013 |   |

OTHER PUBLICATIONS

Escrivá, A. et al., "Determination of liposoluble vitamins in cooked meals, milk and milk products by liquid chromatography," *Journal of Chromatography A*, vol. 947, pp. 313-318, Feb. 2002 (abstract only).

Gleize, B. et al., "Simple and fast HPLC method for simultaneous determination of retinol, tocopherols, coenzyme $Q_{10}$ and carotenoids in complex samples," *Food Chemistry*, vol. 134, pp. 2560-2564, Oct. 2012 (abstract only).

Liu, H-L. et al., "Carotenoids composition in *Scutellaria barbata* D. Don as detected by high performance liquid chromatography-diode array detection-mass spectrometry-atmospheric pressure chemical ionization," *Journal of Functional Food*, vol. 8, pp. 100-110, May 2014 (abstract only).

Martins, P.L.G. et al., "Thermal and light stabilities and antioxidant activity of carotenoids from tomatoes extracted using an ultrasound-assisted completely solvent-free method," *Food Research International*, vol. 82, pp. 156-164, Apr. 2016 (abstract only).

Office Action issued in corresponding Chinese Application No. 201911311503.X, dated Sep. 2, 2020 (14 pages).

Search Report issued in corresponding Chinese Application No. 201911311503.X, dated Aug. 26, 2020 (2 pages).

* cited by examiner

Vitamin A

Vitamin D₂

Vitamin D₃

25-hydroxyvitamin D₂

25-hydroxyvitamin D₃

Vitamin K₁

Vitamin K₂

α-tocopherol

γ-tocopherol

Lutein

Zeaxanthin

β-cryptoxanthin

α-carotene

β-carotene

Lycopene

METHOD FOR SIMULTANEOUSLY DETERMINING FAT-SOLUBLE VITAMINS AND CAROTENOIDS IN SERUM

CROSS REFERENCE TO THE RELATED APPLICATION

The present application claims priority to the Chinese Application No. 201911311503.X, filed on Dec. 18, 2019, which is herein incorporated by reference in its entirety.

TECHNICAL FIELD

The disclosure belongs to the technical field of analytical chemistry, and relates to a method for simultaneously determining fat-soluble vitamins and carotenoids in serum.

BACKGROUND

Fat-soluble nutrients in serum mainly include fat-soluble vitamins and carotenoids. Fat-soluble vitamins mainly include vitamins A, D, E, and K, which all include a ring structure and a long aliphatic hydrocarbon chain, and are insoluble in water or glycerol, but easily soluble in absolute ethanol, methanol, trichloromethane, diethyl ether and oil. Vitamins A and E are common antioxidants, which can prevent readily oxidizable substances such as unsaturated fatty acids (UFAs) in cells from oxidative damage, and protect the cell membrane from being destructed. Vitamin D is a group of secosteroids with anti-rickets effect, also known as the anti-rickets vitamin. Vitamin K is a general term for a class of menadione derivatives, which exhibits physiological functions such as promoting normal blood-clotting. Carotenoids are lipophilic isoprene plant pigments found in red, yellow, orange and dark-green fruits and vegetables. Among more than 750 kinds of carotenoids in the nature, about 15 are found in human serum, and those with a high content in serum include lutein, zeaxanthin, β-cryptoxanthin, α-carotene, β-carotene, lycopene, etc. Carotenoids are efficient antioxidants due to the unsaturated double bonds in the chemical structure thereof. Many fat-soluble nutrients are involved in the homeostatic regulation of whole-body processes closely-related to systemic metabolism, including redox and inflammatory pathways, which are micronutrients necessary to maintain human health. Determining the content of fat-soluble nutrients in serum is very important in researches on nutrition and treatment of cancer or non-cancer related diseases. Therefore, developing a fast and sensitive method to measure the concentration of these nutrients in serum is of great significance for nutritional status assessment, malnutrition diagnosis, intervention program formulation, studies on oxidation or inflammation that may be caused or changed by micronutrients, and the like.

High-performance liquid chromatography (HPLC), an important analytical technique, provides a new method for the detection of various biochemical markers due to its high separation efficiency, high analysis speed, high sensitivity, and small sample volume, which is increasingly used in clinical evaluation. Chinese patents CN105158394A, CN105372374A, CN109030648A, CN105891384B and CN105891384A disclose quantitative analysis methods for various fat-soluble vitamins in serum, milk powder or feed. The pretreatment process uses ethanol to precipitate proteins and then uses a solvent such as n-hexane or petroleum ether for extraction; and the extracts are collected and blow-dried to remove the extractant, then dissolved in methanol, and detected by liquid chromatography (LC) or liquid chromatography-tandem mass spectrometry (LC-MS/MS). The pretreatment process is time-consuming as lots of steps are involved, tends to cause the oxidation of fat-soluble vitamins, and uses a large amount of toxic and harmful reagents. Chinese patents CN108120788A, CN104749293A, CN107561171A, CN105717209A, CN103175934A use tetrahydrofuran (THF), acetone, n-hexane, diethyl ether, ethyl acetate or the like as an extractant to enrich carotenoids in wolfberries, yellow peaches, Chinese rose petals, pepper leaves or strawberries by liquid-liquid extraction (LLE), which are then quantitatively analyzed by LC. In the pretreatment process, the toxic and harmful volatile organic solvent is used at a large amount, which is easy to cause pollution to the environment. Chinese patent CN103175934A adopts a C18 chromatographic column as the stationary phase, which exhibits a limited separation effect on carotenoids with similar structures and isomers thereof. The most typical case is that the C18 chromatographic column cannot separate isomeric lutein and zeaxanthin, so lutein and zeaxanthin are often reported as a whole. In fact, lutein and zeaxanthin are distributed in different areas of the human body and have different functions. Therefore, measuring the concentrations of the two in serum separately will help to study their individual roles. Chinese patent CN108120788A discloses a method for detecting the contents of lutein and zeaxanthin in wolfberries using a C30 chromatographic column as the stationary phase. However, there is currently no patent that discloses a method for simultaneously determining the contents of fat-soluble vitamins and carotenoids in serum.

LLE is a low-cost and readily-operable pretreatment technology, with the selection of an extractant at the core. At present, the organic solvent used for the enrichment of fat-soluble nutrients in serum by LLE has a weak interaction with the nutrients, resulting in a low extraction recovery rate. In order to improve the recovery rate, it is necessary to first precipitate proteins with strong binding to the nutrients and then conduct multiple times of extraction. Therefore, the pretreatment operation is cumbersome and time-consuming as lots of steps are involved, uses the organic solvent at a large amount, and results in relatively-heavy pollution.

SUMMARY

In order to overcome the above-mentioned shortcomings of the prior art, the disclosure is intended to provide a method for simultaneously determining fat-soluble vitamins and carotenoids in serum, which is readily-operable and time-saving, and requires a small amount of extractant.

In order to achieve the above objective, the disclosure adopts the following technical solutions.

The disclosure discloses a method for simultaneously determining fat-soluble vitamins and carotenoids in serum, including: with an ionic liquid (IL) or a binary mixed solvent composed of an IL and an organic solvent as an extractant, pretreating serum by LLE; and with retinyl acetate and trans-β-apo-8'-carotenal as internal standards for fat-soluble vitamins and carotenoids, respectively, subjecting the obtained IL extract phase to HPLC to determine the contents of fat-soluble vitamins and carotenoids in serum.

The fat-soluble vitamins mainly include vitamin A, vitamin D (vitamin $D_2$, vitamin $D_3$, and metabolites of 25-hydroxyvitamin $D_3$ and 25-hydroxyvitamin $D_2$), vitamin E (α-tocopherol and γ-tocopherol), and vitamin K (vitamin $K_1$ and vitamin $K_2$) (FIGS. 1A-1I). The carotenoids mainly include lutein, zeaxanthin, β-cryptoxanthin, α-carotene, β-carotene, lycopene, etc (FIGS. 1J-1O).

Preferably, the IL is composed of two parts: cation $M^+$ and anion $N^-$; the cation $M^+$ is one of imidazole, pyridine, piperidine, pyrrolidine, amine and phosphoric acid cations with one or more substituents, the substituent on the cation $M^+$ includes alkyl, alkenyl or aryl, and when there is a plurality of substituents, the substituents on different positions can be the same or different; and the anion $N^-$ is one of tetrafluoroborate ($BF_4^-$), hexafluorophosphate ($PF_6^-$), and bis(trifluoromethanesulfonyl)imide($Tf_2N^-$).

Preferably, the IL has a mole percent of 1% to 90% in the binary mixed solvent; and the organic solvent is one of dichloromethane (DCM), chloroform, dichloroethane, ethyl acetate, n-butanol, n-heptanol, n-octanol, n-pentane, n-hexane, n-heptane, n-octane, cyclopentane, cyclohexane, petroleum ether with a boiling range of 60° C. to 90° C., petroleum ether with a boiling range of 90° C. to 120° C., and toluene.

The addition of an organic solvent to the IL can reduce the viscosity of the extractant, promote the two-phase transfer process, and reduce the consumption of the IL, thereby resulting in a lower extraction cost.

Preferably, when the pretreatment is conducted by LLE, factors such as the recovery rate of fat-soluble nutrients and the concentration (peak area) of fat-soluble nutrients in the extract are considered comprehensively, with 50 ul to 500 ul of extractant for every 250 ul of serum. The recovery rate of fat-soluble vitamins and carotenoids after a single extraction is 50% to 95%.

The HPLC analysis is conducted at the following conditions: stationary phase: YMC C30 chromatographic column (4.6 mm×250 mm, 5 m); mobile phase A: a methanol aqueous solution with a volume fraction of more than 90%; mobile phase B: a mixed solution of i-propanol/n-hexane with a volume fraction of more than 30%; elution mode: gradient elution, with a flow rate of 1 mL/min; detection wavelength: 324 nm (vitamin A); 263 nm (vitamin D); 290 nm (vitamin E); 254 nm (vitamin K); 450 nm (carotenoid); column temperature: 25° C., and injection volume: 10 μL. The simultaneous determination of fat-soluble vitamins and carotenoids can be completed within 40 min.

By comparing the retention time and the UV-Vis absorption spectrum of each component in serum with that of the internal standard, the to-be-tested fat-soluble vitamins and carotenoids are qualitatively analyzed. Retinyl acetate and trans-β-apo-8'-carotenal are adopted as the internal standards for fat-soluble vitamins and carotenoids, respectively, and the internal standard method is used to establish standard curves. The peak area ratios of the to-be-tested fat-soluble vitamins and carotenoids to the internal standards are compared with standard curves to obtain the contents of fat-soluble vitamins and carotenoids in serum.

The disclosure has the following beneficial effects as compared with the prior art.

In the method for simultaneously determining fat-soluble vitamins and carotenoids in serum disclosed in the disclosure, an IL is first used to pretreat serum by LLE, and then HPLC analysis is conducted to achieve the simultaneous determination of the contents of fat-soluble vitamins and carotenoids in serum. Firstly, compared with traditional solvents, ILs are a new type of green solvents with the following unique properties: (1) with almost no vapor pressure, non-volatility and non-inflammability, the IL is conducive to process safety and environmental protection; (2) the IL exhibits excellent thermal stability and chemical stability; (3) the structure and function can be adjusted, namely, the anion and cation parts of the IL can be designed to achieve a specific functional characteristic; and (4) a variety of intermolecular interaction modes are present, namely, π-π interaction, dipolar interaction, hydrogen bonding and other molecular interactions can all be present and are easy to be adjusted. Therefore, in the disclosure, in view of the multiple intermolecular forces and controllable properties of an IL, an IL or a binary mixed solvent composed of an IL and an organic solvent is adopted as an extractant, which requires no pre-precipitation of proteins, removal of the extractant by blow-drying, and re-dissolving; and after a single extraction, the IL extract phase is directly subjected to HPLC. The pretreatment process is simple and time-saving. Secondly, retinyl acetate and trans-β-apo-8'-carotenal are adopted as the internal standards for fat-soluble vitamins and carotenoids, respectively, and the internal standard method is used to establish standard curves. The peak area ratios of the to-be-tested fat-soluble vitamins and carotenoids to the internal standards are compared with standard curves to obtain the contents of fat-soluble vitamins and carotenoids in serum. It has been verified by experiments that the technical indicators such as sample recovery, detection limit and precision of the method of the disclosure meet requirements, and the accuracy of quantitative results is increased by using the internal standard method, with excellent reproducibility and small error. The determination of the contents of fat-soluble vitamins and carotenoids in serum can be completed within 40 min.

DETAILED DESCRIPTION

To make persons skilled in the art better understand the solutions of the disclosure, the following clearly and completely describes the technical solutions in the examples of the disclosure with reference to the accompanying drawings in the examples of the disclosure. Apparently, the described examples are merely some rather than all of the examples of the disclosure. All other examples obtained by a person of ordinary skill in the art based on the examples of the disclosure without creative efforts shall fall within the protection scope of the disclosure.

Moreover, the terms "include", "comprise", and any other variants mean to cover the non-exclusive inclusion, for example, a process, method, system, product, or device that includes a list of steps or units is not necessarily limited to those steps or units which are clearly listed, but may include other steps or units which are not expressly listed or inherent to such a process, method, system, product, or device.

The disclosure will be further explained in detail below with reference to the accompanying drawings.

The method for simultaneously determining fat-soluble vitamins and carotenoids in serum disclosed in the disclosure includes the following steps:

1) a solution of retinyl acetate and trans-β-apo-8'-carotenal in methanol with a known concentration is added to the to-be-tested serum, and the resulting mixture is well mixed;

2) then an extractant is added to the to-be-tested serum, the resulting mixture is vortexed for 2 min and then centrifuged in a 4° C. centrifuge at 12,000 r/min for 10 min, and the IL extract phase is collected;

3) a certain volume of each of stock solutions for fat-soluble vitamin and carotenoid standards is taken and then diluted with simulated serum to give standard solutions with a series of concentrations, and the standard solutions are treated according to steps 1) and 2) to give the extract phases of the standards; and 4) the serum extract phase and the standard extract phases are analyzed by LC, the internal standard method is adopted to establish standard curves for fat-soluble vitamins and carotenoids, and the peak area ratio of each to-be-tested component in serum to the internal standard is compared with the standard curve to obtain the content of each fat-soluble nutrient in serum.

The fat-soluble vitamins mainly include vitamin A, vitamin D (vitamin $D_2$, vitamin $D_3$, and metabolites of 25-hydroxyvitamin $D_3$ and 25-hydroxyvitamin $D_2$), vitamin E (α-tocopherol and γ-tocopherol), and vitamin K (vitamin $K_1$ and vitamin $K_2$) (FIGS. 1A-1I). The carotenoids mainly include lutein, zeaxanthin, β-cryptoxanthin, α-carotene, β-carotene, lycopene, etc. (FIGS. 1J-1O).

Figure 1A:
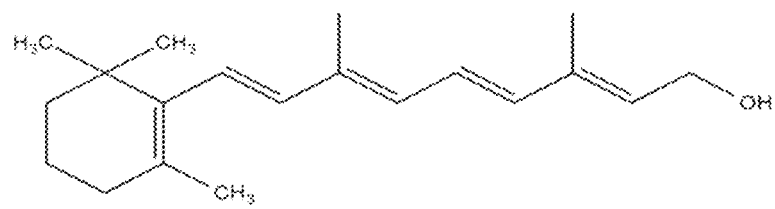
FIGS. 1A-1O are schematic diagrams of the molecular structures of fat-soluble vitamins and carotenoids.
Figure 1B:
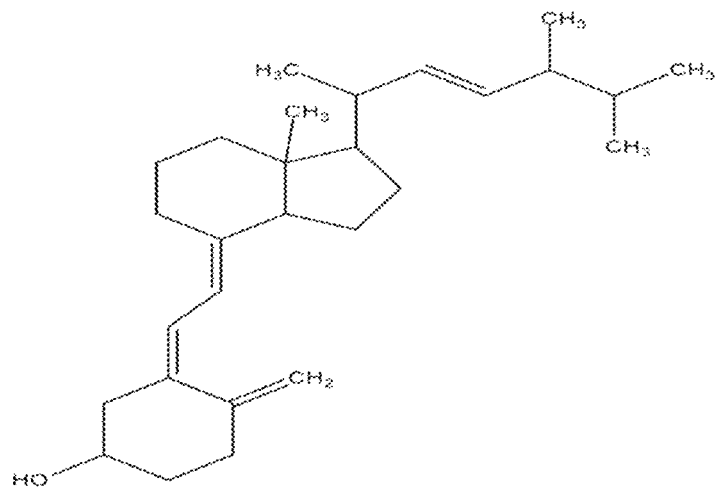
Figure 1C:
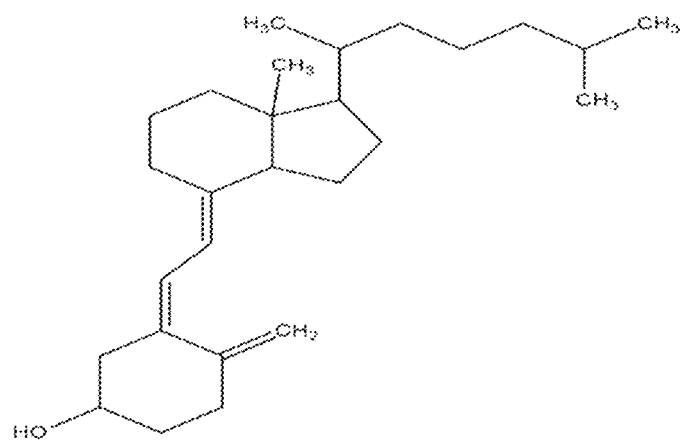
Figure 1D:
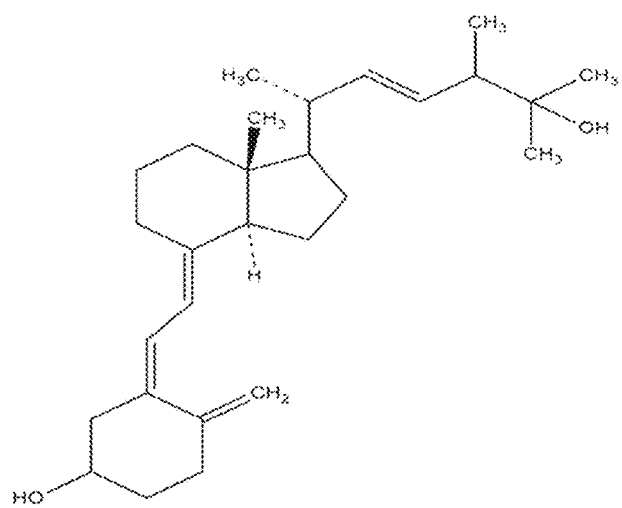
Figure 1E:
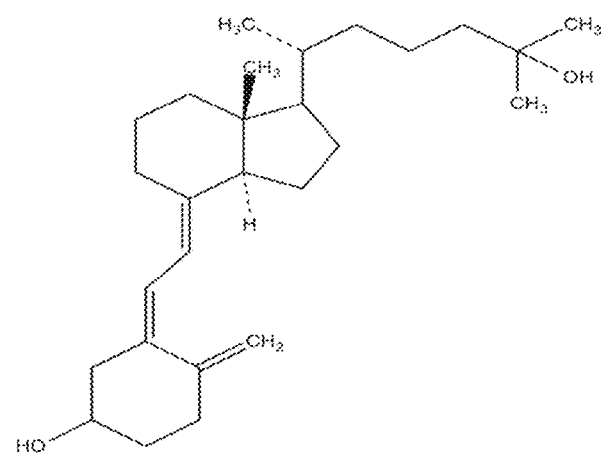
Figure 1F:
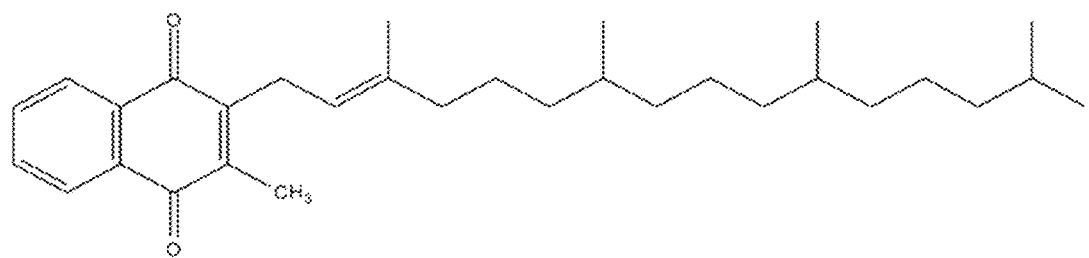
Figure 1G:
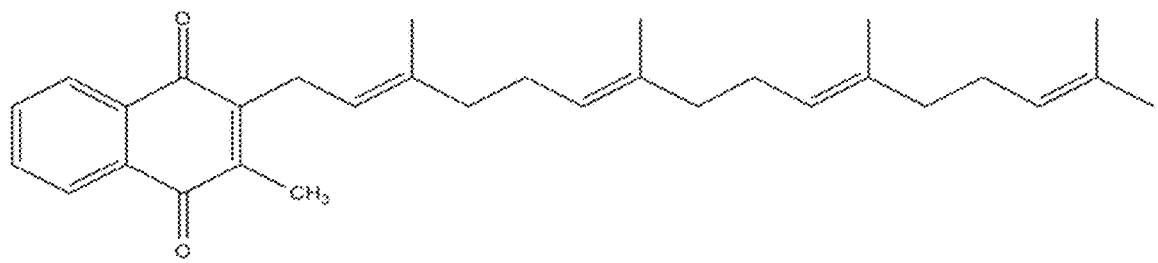
Figure 1H:
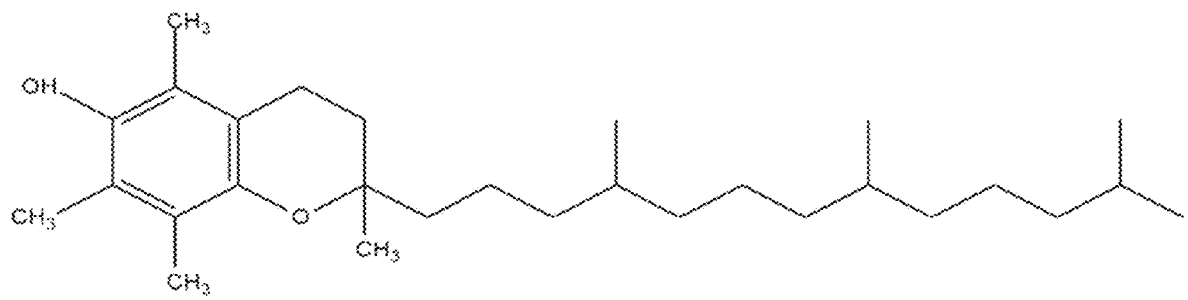
Figure 1I:
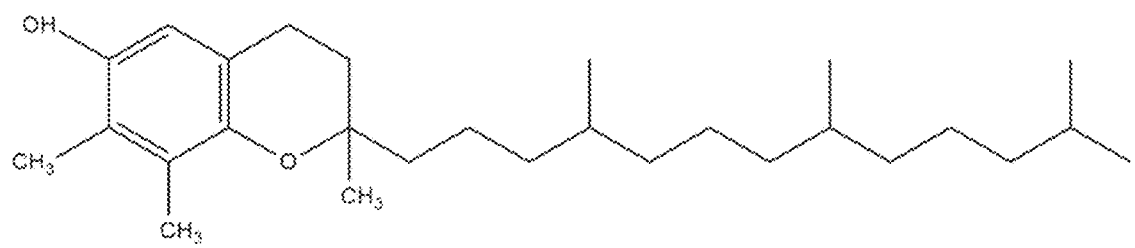
Figure 1J:
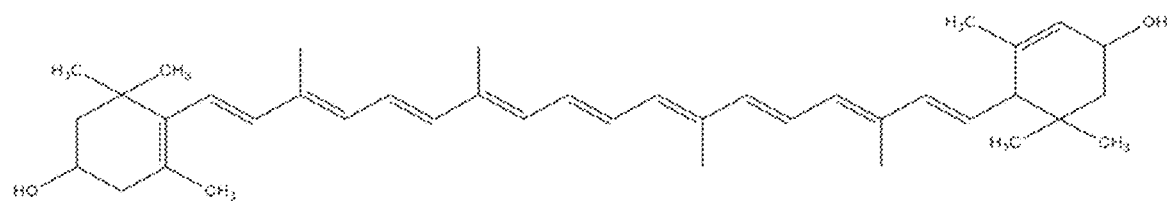
Figure 1K:
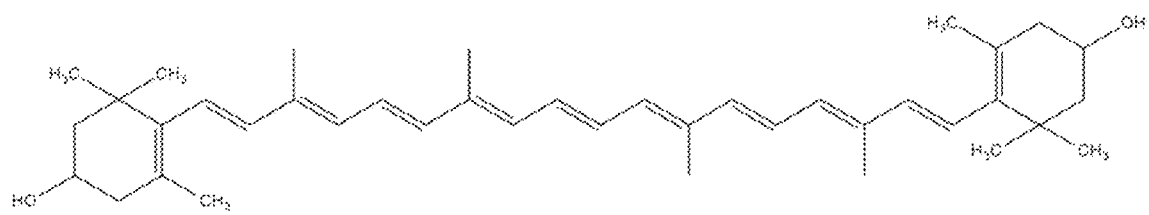
Figure 1L:
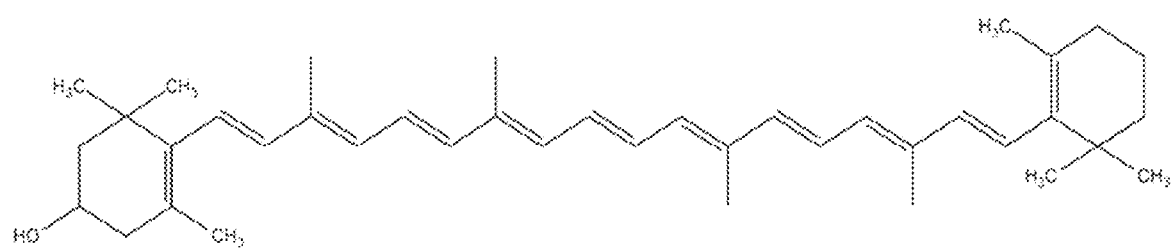
Figure 1M:
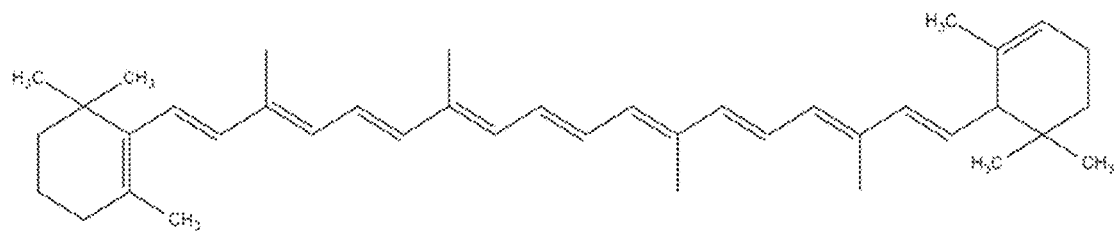
Figure 1N:
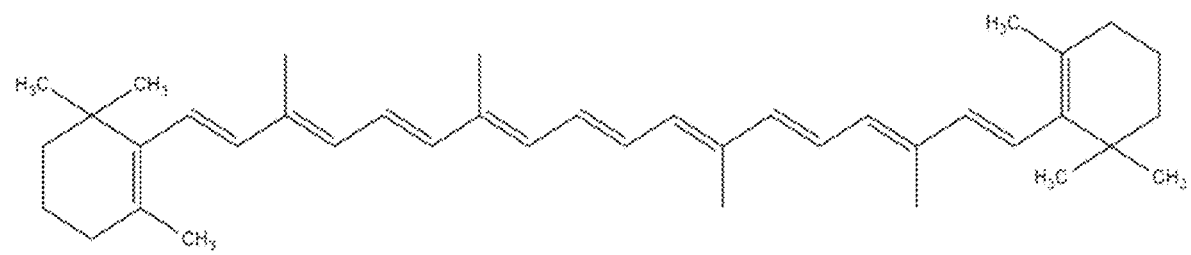
Figure 1O:
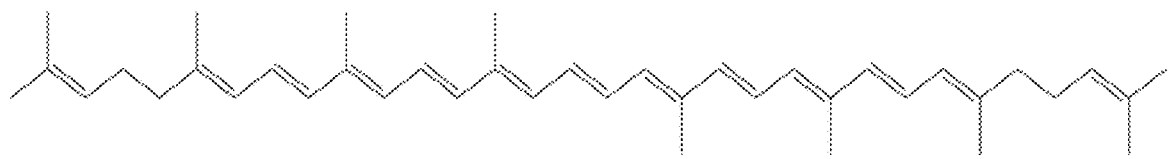
Figure 2:
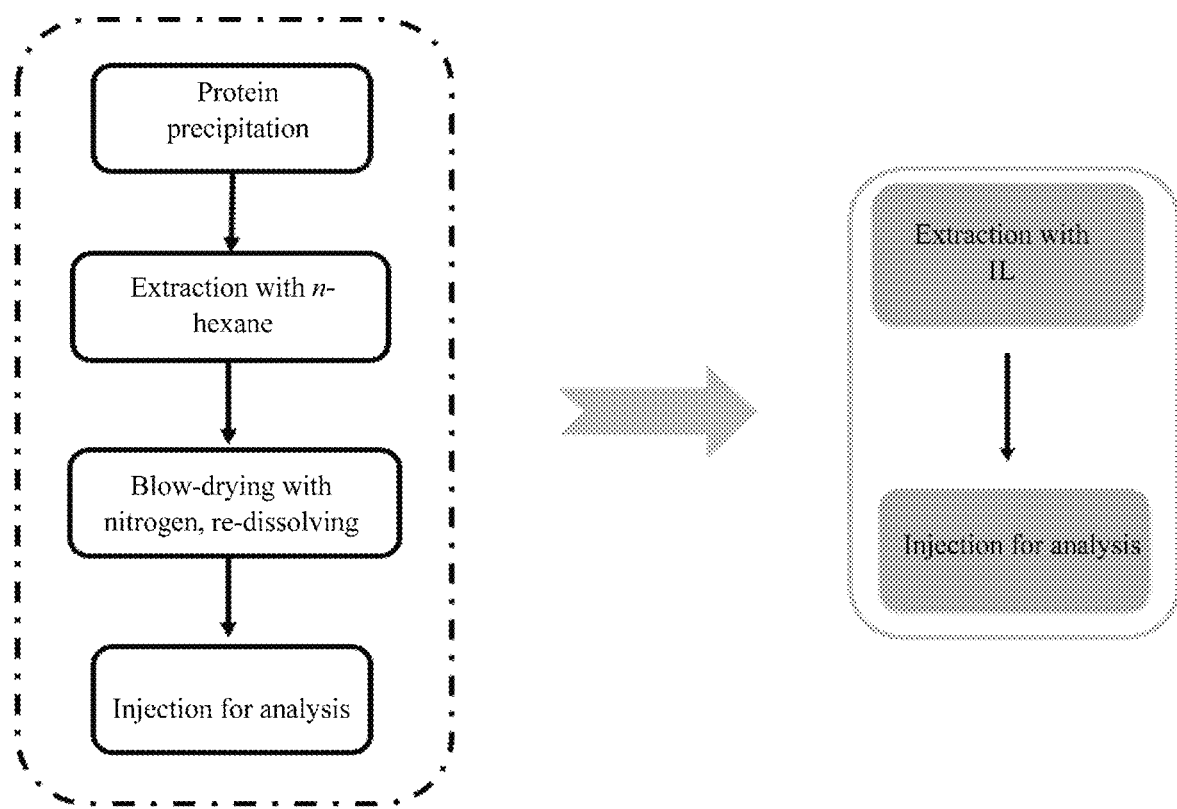
FIG. 2 shows the comparison of the serum sample pretreatment process in the disclosure with the traditional serum sample pretreatment process.
Figure 3A:
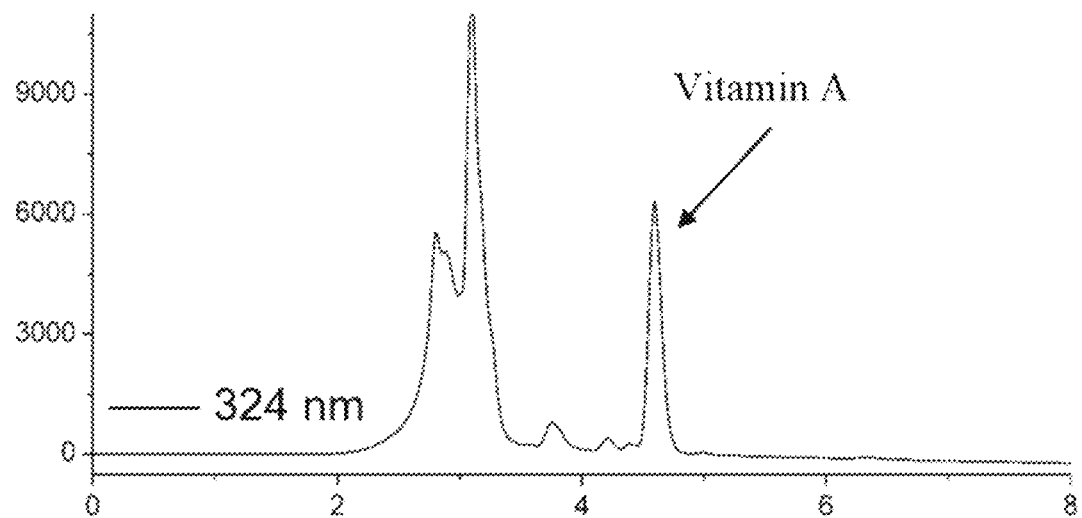
FIGS. 3A-3D shows liquid chromatograms for typical fat-soluble vitamins and carotenoids in serum, where, (a) is for vitamin A; (b) is for 25-hydroxyvitamin $D_3$; (c) is for γ-tocopherol; (d) is for lutein, zeaxanthin, β-cryptoxanthin, α-carotene, β-carotene and lycopene.
Figure 3B:
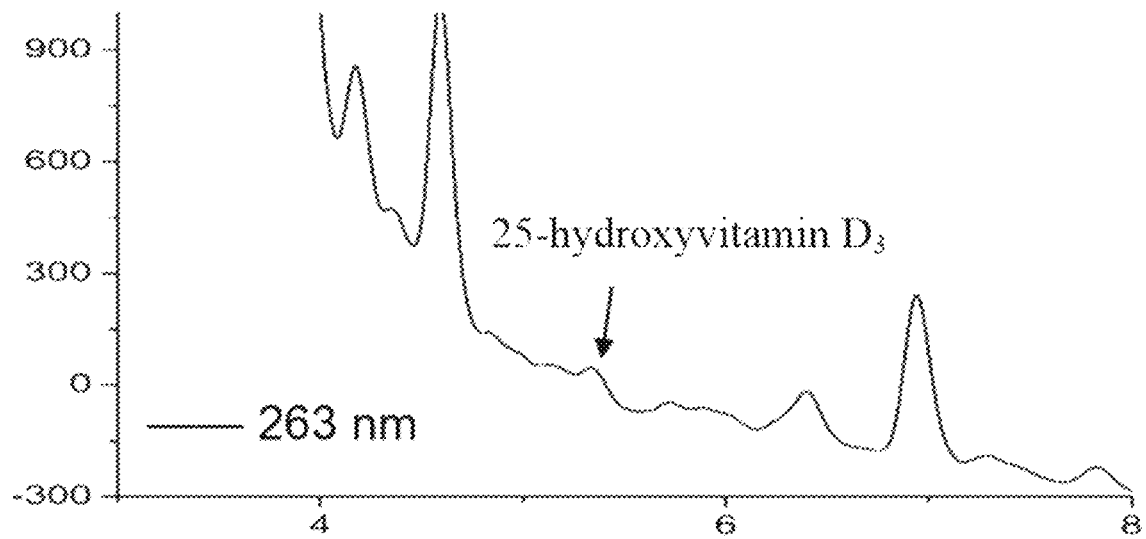
Figure 3C:
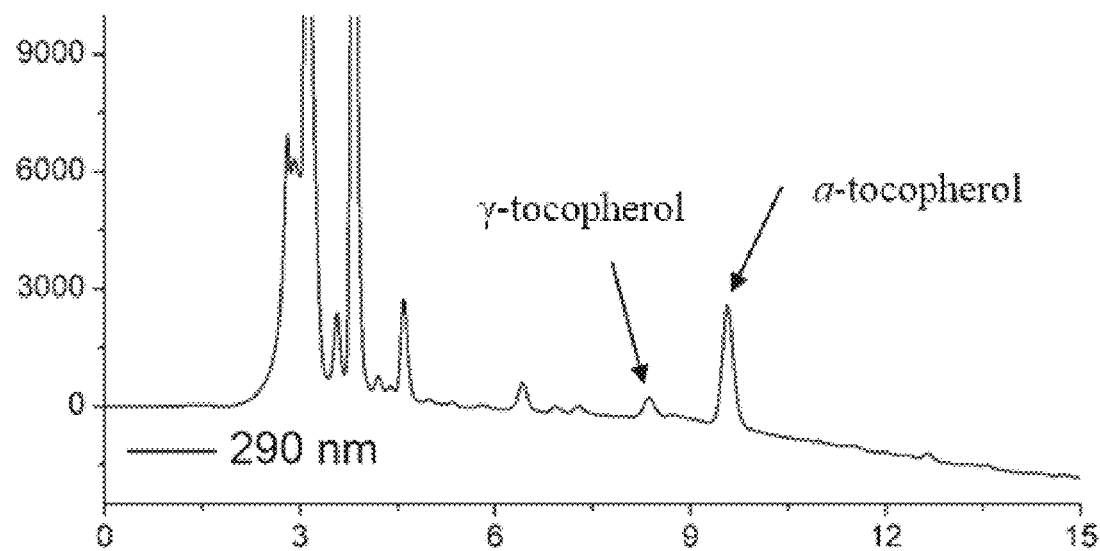
Figure 3D:
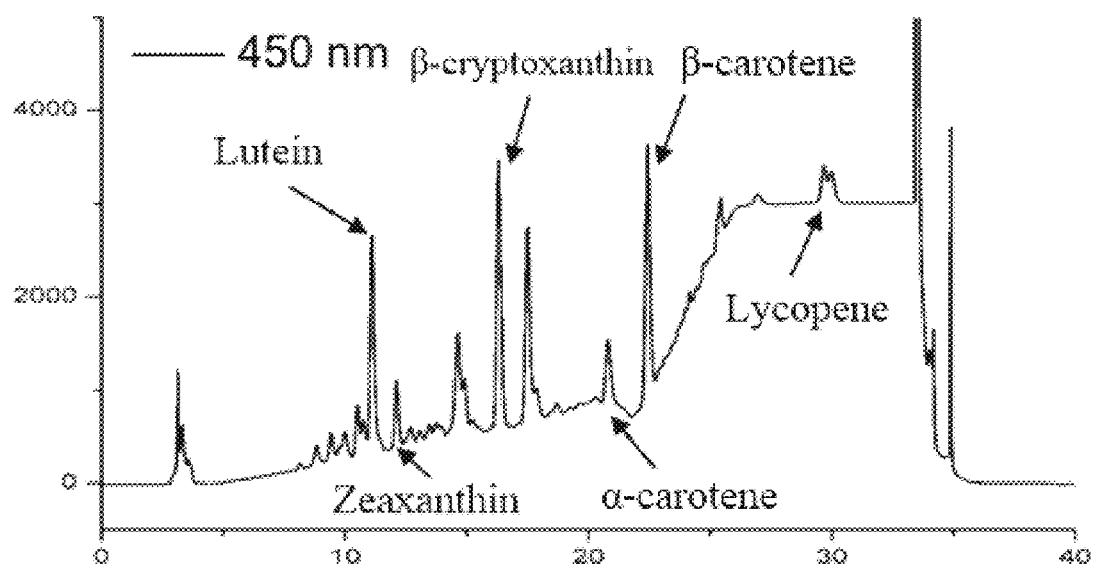

As shown in FIG. 2, compared with the existing methods, the method of the disclosure has the following advantages: The pretreatment process is simple and easy to be conducted, the sample can be prepared in a short time, and the toxic and harmful organic solvent is used at a reduced amount. The HPLC analysis method exhibits an excellent separation effect and a high detection accuracy, and can achieve the simultaneous detection of more than ten fat-soluble nutrients within 40 min (the HPLC chromatograms of typical fat-soluble vitamins and carotenoids in serum are shown in FIGS. 3A-3D). Moreover, with high-throughput and low-cost, the disclosure can be easily generalized in clinics.

Example 1

A method for simultaneously determining fat-soluble vitamins and carotenoids in serum included the following steps:

1) 5 uL of a solution of retinyl acetate and trans-β-apo-8'-carotenal in methanol with a known concentration was added to 250 uL of serum, and the resulting mixture was well mixed;

2) then 100 uL of a solution of 1-butyl-3-methylimidazolium bis[(trifluoromethyl)sulfonyl]imide ([bmim][$Tf_2N$]) in n-hexane with a mole fraction of 50% was added to the serum, the resulting mixture was vortexed for 2 min and then centrifuged in a 4° C. centrifuge at 12,000 r/min for 10 min, and the TL extract phase was collected;

3) a certain volume of each of stock solutions for fat-soluble vitamin and carotenoid standards was taken and then diluted with simulated serum to give standard solutions with a series of concentrations, and 250 uL of each of the standard solutions was taken and treated according to steps 1) and 2) to give the extract phases of the standards; and 4) the serum extract phase and the standard extract phases were analyzed by LC, the internal standard method was adopted to establish standard curves for fat-soluble vitamins and carotenoids, and the peak area ratio of each to-be-tested component in serum to the internal standard was compared with the standard curve to obtain the content of each fat-soluble nutrient in serum. The HPLC analysis was conducted at the following conditions: chromatographic column: YMC C30 (4.6 mm×250 mm, 5 m); mobile phase A: methanol; mobile phase B: a mixed solution of i-propanol/n-hexane with a volume fraction of 30%; flow rate: 1 mL/min; elution mode: gradient elution (0 min to 20 min, 100% A to 50% A; 20 min to 22 min, 50% A to 0% A; 22 min to 30 min, 0% A to 0% A; 30 min to 31 min, 0% A to 100% A); multi-wavelength detection (324 nm for vitamin A; 263 nm for vitamin D; 290 nm for vitamin E; 254 nm for vitamin K; and 450 nm for carotenoid); column temperature: 25° C., and injection volume: 10 μL.

This quantitative analysis method is accurate and reliable. The sample recovery rate of the detected fat-soluble vitamins and carotenoids is 83.2% to 108.5%, and the minimum detection limit is 0.005 ug/mL to 0.025 ug/mL. As detected by the experiment, the contents of vitamin A, 25-hydroxyvitamin $D_3$, α-tocopherol, γ-tocopherol, lutein, zeaxanthin, β-cryptoxanthin, α-carotene, β-carotene and lycopene in the serum of 20 normal people are 1.05±0.23 μmol/L, 0.051±0.036 μmol/L, 34.2±10.8 μmol/L, 4.14±0.9 μmol/L, 0.48±0.24 μmol/L, 0.072±0.026 μmol/L, 0.16±0.14 μmol/L, 0.073±0.057 μmol/L, 0.53±0.37 μmol/L, and 0.17±0.12 μmol/L, respectively, which are consistent with the content ranges of these nutrients in a normal person reported in references.

Example 2

A method for simultaneously determining fat-soluble vitamins and carotenoids in serum included the following steps:

1) 15 uL of a solution of retinyl acetate and trans-β-apo-8'-carotenal in methanol with a known concentration was added to 250 uL of serum, and the resulting mixture was well mixed;

2) then 50 uL of a solution of 1-hexyl-3-methylimidazolium tetrafluoroborate ([hmim][$BF_4$]) in DCM with a mole fraction of 30% was added to the serum, the resulting mixture was vortexed for 2 min and then centrifuged in a 4° C. centrifuge at 12,000 r/min for 10 min, and the L extract phase was collected;

3) a certain volume of each of stock solutions for fat-soluble vitamin and carotenoid standards was taken and then diluted with simulated serum to give standard solutions with a series of concentrations, and 250 uL of each of the standard solutions was taken and treated according to steps 1) and 2) to give the extract phases of the standards; and 4) the serum extract phase and the standard extract phases were analyzed by LC, the internal standard method was adopted to establish standard curves for fat-soluble vitamins and carotenoids, and the peak area ratio of each to-be-tested component in serum to the internal standard was compared with the standard curve to obtain the content of each fat-soluble nutrient in serum.

The HPLC analysis was conducted at the following conditions: chromatographic column: YMC C30; mobile phase A: a methanol aqueous solution with a volume fraction of 90%; mobile phase B: a mixed solution of i-propanol/n-hexane with a volume fraction of 40%; flow rate: 1 mL/min; elution mode: gradient elution (0 min to 15 min, 100% A to 40% A; 15 min to 18 min, 40% A to 0% A; 18 min to 23 min, 0% A to 0% A; 23 min to 25 min, 0% A to 100% A); multi-wavelength detection (324 nm for vitamin A; 263 nm for vitamin D; 290 nm for vitamin E; 254 nm for vitamin K; and 450 nm for carotenoid); column temperature: 25° C., and injection volume: 10 µL.

This quantitative analysis method is accurate and reliable. The sample recovery rate of the detected fat-soluble vitamins and carotenoids is 89.8% to 110.2%, and the minimum detection limit is 0.005 ug/mL to 0.025 ug/mL. As detected by the experiment, the contents of vitamin A, 25-hydroxyvitamin $D_3$, α-tocopherol, γ-tocopherol, lutein, zeaxanthin, β-cryptoxanthin, α-carotene, β-carotene and lycopene in the serum of 30 normal people are 2.45±0.53 µmol/L, 0.068±0.04 µmol/L, 39.1±14.7 µmol/L, 2.96±0.77 µmol/L, 0.64±0.31 µmol/L, 0.13±0.09 µmol/L, 0.089±0.067 µmol/L, 0.046±0.033 µmol/L, 0.44±0.34 µmol/L, and 0.21±0.14 µmol/L, respectively, which are consistent with the content ranges of these nutrients in a normal person reported in references.

Example 3

A method for simultaneously determining fat-soluble vitamins and carotenoids in serum included the following steps:

1) 10 uL of a solution of retinyl acetate and trans-β-apo-8'-carotenal in methanol with a known concentration was added to 250 uL of serum, and the resulting mixture was well mixed;

2) then 200 uL of a solution of N-dodecylpyridinium hexafluorophosphate ($[C_{12}Py][PF_6]$) in toluene with a mole fraction of 40% was added to the serum, the resulting mixture was vortexed for 2 min and then centrifuged in a 4° C. centrifuge at 12,000 r/min for 10 min, and the L extract phase was collected;

3) a certain volume of each of stock solutions for fat-soluble vitamin and carotenoid standards was taken and then diluted with simulated serum to give standard solutions with a series of concentrations, and 250 uL of each of the standard solutions was taken and treated according to steps 1) and 2) to give the L extract phases of the standards; and 4) the serum extract phase and the standard extract phases were analyzed by LC, the internal standard method was adopted to establish standard curves for fat-soluble vitamins and carotenoids, and the peak area ratio of each to-be-tested component in serum to the internal standard was compared with the standard curve to obtain the content of each fat-soluble nutrient in serum.

The HPLC analysis was conducted at the following conditions: chromatographic column: YMC C30; mobile phase A: a methanol aqueous solution with a volume fraction of 95%; mobile phase B: a mixed solution of i-propanol/n-hexane with a volume fraction of 50%; flow rate: 1 mL/min; elution mode: gradient elution (0 min to 30 min, 100% A to 10% A; 30 min to 32 min, 10% A to 10% A; 32 min to 33 min, 10% A to 100% A); multi-wavelength detection (324 nm for vitamin A; 263 nm for vitamin D; 290 nm for vitamin E; 254 nm for vitamin K; and 450 nm for carotenoid); column temperature: 25° C., and injection volume: 10 µL.

This quantitative analysis method is accurate and reliable. The sample recovery rate of the detected fat-soluble vitamins and carotenoids is 90.3% to 99.5%, and the minimum detection limit is 0.005 ug/mL to 0.025 ug/mL. As detected by the experiment, the contents of vitamin A, 25-hydroxyvitamin $D_3$, α-tocopherol, γ-tocopherol, lutein, zeaxanthin, β-cryptoxanthin, α-carotene, β-carotene and lycopene in the serum of 50 normal people are 1.88±0.43 µmol/L, 0.13±0.08 µmol/L, 38.9±14.2 µmol/L, 5.66±1.7 µmol/L, 0.61±0.16 µmol/L, 0.089±0.02 µmol/L, 0.14±0.03 µmol/L, 0.038±0.017 µmol/L, 0.62±0.45 µmol/L, and 0.19±0.13 µmol/L, respectively, which are consistent with the content ranges of these nutrients in a normal person reported in references.

Example 4

A method for simultaneously determining fat-soluble vitamins and carotenoids in serum included the following steps:

1) 20 uL of a solution of retinyl acetate and trans-β-apo-8'-carotenal in methanol with a known concentration was added to 250 uL of serum, and the resulting mixture was well mixed;

2) then 150 uL of a solution of 1-benzyl-3-methylimidazolium hexafluorophosphate ($[bzmim][PF_6]$) in cyclopentane with a mole fraction of 70% was added to the serum, the resulting mixture was vortexed for 2 min and then centrifuged in a 4° C. centrifuge at 12,000 r/min for 10 min, and the IL extract phase was collected;

3) a certain volume of each of methanol stock solutions for fat-soluble vitamin and carotenoid standards was taken and then diluted with simulated serum to give standard solutions with a series of concentrations, and 250 uL of each of the standard solutions was taken and treated according to steps 1) and 2) to give the IL extract phases of the standards; and 4) the serum extract phase and the standard extract phases were analyzed by LC, the internal standard method was adopted to establish standard curves for fat-soluble vitamins and carotenoids, and the peak area ratio of each to-be-tested component in serum to the internal standard was compared with the standard curve to obtain the content of each fat-soluble nutrient in serum.

The HPLC analysis was conducted at the following conditions: chromatographic column: YMC C30; mobile phase A: a methanol aqueous solution with a volume fraction of 98%; mobile phase B: a mixed solution of i-propanol/n-hexane with a volume ratio of 7/3; flow rate: 1 mL/min; elution mode: gradient elution (0 min to 25 min, 100% A to 0% A; 25 min to 35 min, 0% A to 100% A); multi-wavelength detection (324 nm for vitamin A; 263 nm for vitamin D; 290 nm for vitamin E; 254 nm for vitamin K; and 450 nm for carotenoid); column temperature: 25° C., and injection volume: 10 µL.

This quantitative analysis method is accurate and reliable. The sample recovery rate of the detected fat-soluble vitamins and carotenoids is 86.5% to 112.3%, and the minimum detection limit is 0.005 ug/mL to 0.025 ug/mL. As detected by the experiment, the contents of vitamin A, 25-hydroxyvitamin $D_3$, α-tocopherol, γ-tocopherol, lutein, zeaxanthin, β-cryptoxanthin, α-carotene, β-carotene and lycopene in the serum of 40 normal people are 0.75±0.26 µmol/L, 0.098±0.03 µmol/L, 33.3±11.1 µmol/L, 6.23±0.61 µmol/L, 0.70±0.34 µmol/L, 0.065±0.022 µmol/L, 0.12±0.05 µmol/L, 0.039±0.015 µmol/L, 0.59±0.31 µmol/L, and 0.11±0.092 µmol/L, respectively, which are consistent with the content ranges of these nutrients in a normal person reported in references.

Example 5

A method for simultaneously determining fat-soluble vitamins and carotenoids in serum included the following steps:

1) 15 uL of a solution of retinyl acetate and trans-β-apo-8'-carotenal in methanol with a known concentration was added to 250 uL of serum, and the resulting mixture was well mixed;

2) then 400 uL of a solution of N-octyl-N-methylpyrrolidinium bis(trifluoromethylsulfonyl)imide ([OPyr][Tf$_2$N]) in ethyl acetate with a mole fraction of 10% was added to the serum, the resulting mixture was vortexed for 2 min and then centrifuged in a 4° C. centrifuge at 12,000 r/min for 10 min, and the IL extract phase was collected;

3) a certain volume of each of methanol stock solutions for fat-soluble vitamin and carotenoid standards was taken and then diluted with simulated serum to give standard solutions with a series of concentrations, and 250 uL of each of the standard solutions was taken and treated according to steps 1) and 2) to give the IL extract phases of the standards; and 4) the serum extract phase and the standard extract phases were analyzed by LC, the internal standard method was adopted to establish standard curves for fat-soluble vitamins and carotenoids, and the peak area ratio of each to-be-tested component in serum to the internal standard was compared with the standard curve to obtain the content of each fat-soluble nutrient in serum.

The HPLC analysis was conducted at the following conditions: chromatographic column: YMC C30; mobile phase A: methanol; mobile phase B: a mixed solution of i-propanol/n-hexane with a volume fraction of 60%; flow rate: 1 mL/min; elution mode: gradient elution (0 min to 10 min, 100% A to 85% A; 10 min to 25 min, 85% A to 0% A; 25 min to 30 min, 0% A to 100% A); multi-wavelength detection (324 nm for vitamin A; 263 nm for vitamin D; 290 nm for vitamin E; 254 nm for vitamin K; and 450 nm for carotenoid); column temperature: 25° C., and injection volume: 10 μL.

This quantitative analysis method is accurate and reliable. The sample recovery rate of the detected fat-soluble vitamins and carotenoids is 80.3% to 98.2%, and the minimum detection limit is 0.005 ug/mL to 0.025 ug/mL. As detected by the experiment, the contents of vitamin A, 25-hydroxyvitamin D$_3$, α-tocopherol, γ-tocopherol, lutein, zeaxanthin, β-cryptoxanthin, α-carotene, β-carotene and lycopene in the serum of 60 normal people are 2.58±0.70 μmol/L, 0.034±0.026 μmol/L, 35.2±4.8 μmol/L, 3.14±0.6 μmol/L, 0.62±0.18 μmol/L, 0.042±0.017 μmol/L, 0.10±0.09 μmol/L, 0.044±0.033 μmol/L, 0.59±0.31 μmol/L, and 0.11±0.06 μmol/L, respectively, which are consistent with the content ranges of these nutrients in a normal person reported in references.

Example 6

A method for simultaneously determining fat-soluble vitamins and carotenoids in serum included the following steps:

1) 5 uL of a solution of retinyl acetate and trans-β-apo-8'-carotenal in methanol with a known concentration was added to 250 uL of serum, and the resulting mixture was well mixed;

2) then 100 uL of a solution of tetrabutylammonium bis(trifluoromethylsulfonyl)imide ([N$_{4,4,4,4}$][Tf$_2$N]) in n-octanol with a mole fraction of 60% was added to the serum, the resulting mixture was vortexed for 2 min and then centrifuged in a 4° C. centrifuge at 12,000 r/min for 10 min, and the IL extract phase was collected;

3) a certain volume of each of stock solutions for fat-soluble vitamin and carotenoid standards was taken and then diluted with simulated serum to give standard solutions with a series of concentrations, and 250 uL of each of the standard solutions was taken and treated according to steps 1) and 2) to give the IL extract phases of the standards; and 4) the serum extract phase and the standard extract phases were analyzed by LC, the internal standard method was adopted to establish standard curves for fat-soluble vitamins and carotenoids, and the peak area ratio of each to-be-tested component in serum to the internal standard was compared with the standard curve to obtain the content of each fat-soluble nutrient in serum.

The HPLC analysis was conducted at the following conditions: chromatographic column: YMC C30; mobile phase A: a methanol aqueous solution with a volume fraction of 98%; mobile phase B: i-propanol; flow rate: 1 mL/min; elution mode: gradient elution (0 min to 10 min, 100% A to 70% A; 10 min to 20 min, 70% A to 0% A; 20 min to 30 min, 0% A to 100% A); multi-wavelength detection (324 nm for vitamin A; 263 nm for vitamin D; 290 nm for vitamin E; 254 nm for vitamin K; and 450 nm for carotenoid); column temperature: 25° C., and injection volume: 10 μL.

This quantitative analysis method is accurate and reliable. The sample recovery rate of the detected fat-soluble vitamins and carotenoids is 93.2% to 105.8%, and the minimum detection limit is 0.005 ug/mL to 0.025 ug/mL. As detected by the experiment, the contents of vitamin A, 25-hydroxyvitamin D$_3$, α-tocopherol, γ-tocopherol, lutein, zeaxanthin, β-cryptoxanthin, α-carotene, β-carotene and lycopene in the serum of 35 normal people are 2.05±0.66 μmol/L, 0.048±0.04 μmol/L, 35.2±7.8 μmol/L, 5.06±1.0 μmol/L, 0.46±0.12 μmol/L, 0.063±0.039 μmol/L, 0.12±0.05 μmol/L, 0.030±0.019 μmol/L, 0.44±0.19 μmol/L, and 0.43±0.25 μmol/L, respectively, which are consistent with the content ranges of these nutrients in a normal person reported in references.

Example 7

A method for simultaneously determining fat-soluble vitamins and carotenoids in serum included the following steps:

1) 20 uL of a solution of retinyl acetate and trans-β-apo-8'-carotenal in methanol with a known concentration was added to 250 uL of serum, and the resulting mixture was well mixed;

2) then 80 uL of a solution of N-hexadecyl-N-methylpiperidinium hexafluorophosphate ([C$_{16}$MPip][PF$_6$]) in petroleum ether (boiling range: 60° C. to 90° C.) with a mole fraction of 50% was added to the serum, the resulting mixture was vortexed for 2 min and then centrifuged in a 4° C. centrifuge at 12,000 r/min for 10 min, and the IL extract phase was collected;

3) a certain volume of each of stock solutions for fat-soluble vitamin and carotenoid standards was taken and then diluted with simulated serum to give standard solutions with a series of concentrations, and 250 uL of each of the standard solutions was taken and treated according to steps 1) and 2) to give the L extract phases of the standards; and 4) the serum extract phase and the standard extract phases were analyzed by LC, the internal standard method was adopted to establish standard curves for fat-soluble vitamins and carotenoids, and the peak area ratio of each to-be-tested component in serum to the internal standard was compared with the standard curve to obtain the content of each fat-soluble nutrient in serum.

The HPLC analysis was conducted at the following conditions: chromatographic column: YMC C30; mobile phase A: a methanol aqueous solution with a volume fraction of 93%; mobile phase B: a mixed solution of i-propanol/n-hexane with a volume fraction of 80%; flow rate: 1 mL/min; elution mode: gradient elution (0 min to 20 min, 100% A to 50% A; 20 min to 23 min, 50% A to 0% A; 23 min to 30 min, 0% A to 100% A); multi-wavelength detection (324 nm for vitamin A; 263 nm for vitamin D; 290 nm for vitamin E; 254 nm for vitamin K; and 450 nm for carotenoid); column temperature: 25° C., and injection volume: 10 μL.

This quantitative analysis method is accurate and reliable. The sample recovery rate of the detected fat-soluble vitamins and carotenoids is 90.4% to 113.5%, and the minimum detection limit is 0.005 ug/mL to 0.025 ug/mL. As detected by the experiment, the contents of vitamin A, 25-hydroxyvitamin $D_3$, α-tocopherol, γ-tocopherol, lutein, zeaxanthin, β-cryptoxanthin, α-carotene, β-carotene and lycopene in the serum of 40 normal people are 1.63±0.35 μmol/L, 0.058±0.045 μmol/L, 30.2±8.2 μmol/L, 3.45±1.2 μmol/L, 0.61±0.16 μmol/L, 0.067±0.036 μmol/L, 0.14±0.03 μmol/L, 0.06±0.06 μmol/L, 0.62±0.45 μmol/L, and 0.07±0.03 μmol/L, respectively, which are consistent with the content ranges of these nutrients in a normal person reported in references.

Example 8

A method for simultaneously determining fat-soluble vitamins and carotenoids in serum included the following steps:

1) 15 uL of a solution of retinyl acetate and trans-β-apo-8'-carotenal in methanol with a known concentration was added to 250 uL of serum, and the resulting mixture was well mixed;

2) then 120 uL of a solution of N-octylpyridinium tetrafluoroborate ([OPy][BF$_4$]) in cyclohexane with a mole fraction of 10% was added to the serum, the resulting mixture was vortexed for 2 min and then centrifuged in a 4° C. centrifuge at 12,000 r/min for 10 min, and the IL extract phase was collected;

3) a certain volume of each of stock solutions for fat-soluble vitamin and carotenoid standards was taken and then diluted with simulated serum to give standard solutions with a series of concentrations, and 250 uL of each of the standard solutions was taken and treated according to steps 1) and 2) to give the IL extract phases of the standards; and 4) the serum extract phase and the standard extract phases were analyzed by LC, the internal standard method was adopted to establish standard curves for fat-soluble vitamins and carotenoids, and the peak area ratio of each to-be-tested component in serum to the internal standard was compared with the standard curve to obtain the content of each fat-soluble nutrient in serum.

The HPLC analysis was conducted at the following conditions: chromatographic column: YMC C30; mobile phase A: a methanol aqueous solution with a volume fraction of 97%; mobile phase B: a mixed solution of i-propanol/n-hexane with a volume fraction of 90%; flow rate: 1 mL/min; elution mode: gradient elution (0 min to 18 min, 100% A to 40% A; 18 min to 25 min, 40% A to 0% A; 25 min to 33 min, 0% A to 100% A); multi-wavelength detection (324 nm for vitamin A; 263 nm for vitamin D; 290 nm for vitamin E; 254 nm for vitamin K; and 450 nm for carotenoid); column temperature: 25° C., and injection volume: 10 μL.

This quantitative analysis method is accurate and reliable. The sample recovery rate of the detected fat-soluble vitamins and carotenoids is 84.3% to 97.5%, and the minimum detection limit is 0.005 ug/mL to 0.025 ug/mL. As detected by the experiment, the contents of vitamin A, 25-hydroxyvitamin $D_3$, α-tocopherol, γ-tocopherol, lutein, zeaxanthin, β-cryptoxanthin, α-carotene, β-carotene and lycopene in the serum of 60 normal people are 1.91±0.12 μmol/L, 0.068±0.04 mol/L, 35.6±13.1 μmol/L, 3.28±1.7 μmol/L, 0.46±0.12 μmol/L, 0.042±0.023 μmol/L, 0.21±0.05 μmol/L, 0.063±0.042 μmol/L, 0.85±0.27 μmol/L, and 0.28±0.09 μmol/L, respectively, which are consistent with the content ranges of these nutrients in a normal person reported in references.

Example 9

A method for simultaneously determining fat-soluble vitamins and carotenoids in serum included the following steps:

1) 10 uL of a solution of retinyl acetate and trans-β-apo-8'-carotenal in methanol with a known concentration was added to 250 uL of serum, and the resulting mixture was well mixed;

2) then 500 uL of a solution of hexadecyl trimethylphosphonium hexafluorophosphate ([P1,1,1,16][PF$_6$]) in n-heptanol with a mole fraction of 20% was added to the serum, the resulting mixture was vortexed for 2 min and then centrifuged in a 4° C. centrifuge at 12,000 r/min for 10 min, and the IL extract phase was collected;

3) a certain volume of each of stock solutions for fat-soluble vitamin and carotenoid standards was taken and then diluted with simulated serum to give standard solutions with a series of concentrations, and 250 uL of each of the standard solutions was taken and treated according to steps 1) and 2) to give the IL extract phases of the standards; and 4) the serum extract phase and the standard extract phases were analyzed by LC, the internal standard method was adopted to establish standard curves for fat-soluble vitamins and carotenoids, and the peak area ratio of each to-be-tested component in serum to the internal standard was compared with the standard curve to obtain the content of each fat-soluble nutrient in serum.

The IPLC analysis was conducted at the following conditions: chromatographic column: YMC C30; mobile phase A: a methanol aqueous solution with a volume fraction of 96%; mobile phase B: a mixed solution of i-propanol/n-hexane with a volume fraction of 65%; flow rate: 1 mL/min; elution mode: gradient elution (0 min to 25 min, 100% A to 0% A; 25 min to 28 min, 0% A to 100% A); multi-wavelength detection (324 nm for vitamin A; 263 nm for vitamin D; 290 nm for vitamin E; 254 nm for vitamin K; and 450 nm for carotenoid); column temperature: 25° C., and injection volume: 10 μL.

This quantitative analysis method is accurate and reliable. The sample recovery rate of the detected fat-soluble vitamins and carotenoids is 85.4% to 100.3%, and the minimum detection limit is 0.005 ug/mL to 0.025 ug/mL. As detected by the experiment, the contents of vitamin A, 25-hydroxyvitamin $D_3$, α-tocopherol, γ-tocopherol, lutein, zeaxanthin, β-cryptoxanthin, α-carotene, β-carotene and lycopene in the serum of 70 normal people are 3.41±0.53 μmol/L, 0.081±0.04 μmol/L, 44.2±12.6 μmol/L, 7.14±2.45 μmol/L, 0.33±0.14 μmol/L, 0.052±0.046 μmol/L, 0.13±0.08 μmol/L, 0.062±0.037 μmol/L, 0.72±0.35 μmol/L, and 0.32±0.04

μmol/L, respectively, which are consistent with the content ranges of these nutrients in a normal person reported in references.

Example 10

A method for simultaneously determining fat-soluble vitamins and carotenoids in serum included the following steps:

1) 20 uL of a solution of retinyl acetate and trans-β-apo-8'-carotenal in methanol with a known concentration was added to 250 uL of serum, and the resulting mixture was well mixed;

2) then 200 uL of a solution of N-butyl-N-methylpiperidinium bis(trifluoromethylsulfonyl)imide ([BMPip][Tf$_2$N]) in dichloroethane with a mole fraction of 35% was added to the serum, the resulting mixture was vortexed for 2 min and then centrifuged in a 4° C. centrifuge at 12,000 r/min for 10 min, and the IL extract phase was collected;

3) a certain volume of each of stock solutions for fat-soluble vitamin and carotenoid standards was taken and then diluted with simulated serum to give standard solutions with a series of concentrations, and 250 uL of each of the standard solutions was taken and treated according to steps 1) and 2) to give the IL extract phases of the standards; and 4) the serum extract phase and the standard extract phases were analyzed by LC, the internal standard method was adopted to establish standard curves for fat-soluble vitamins and carotenoids, and the peak area ratio of each to-be-tested component in serum to the internal standard was compared with the standard curve to obtain the content of each fat-soluble nutrient in serum.

The HPLC analysis was conducted at the following conditions: chromatographic column: YMC C30; mobile phase A: methanol; mobile phase B: a mixed solution of i-propanol/n-hexane with a volume fraction of 40%; flow rate: 1 mL/min; elution mode: gradient elution (0 min to 16 min, 100% A to 40% A; 16 min to 20 min, 40% A to 0% A; 20 min to 25 min, 0% A to 100% A); multi-wavelength detection (324 nm for vitamin A; 263 nm for vitamin D; 290 nm for vitamin E; 254 nm for vitamin K; and 450 nm for carotenoid); column temperature: 25° C., and injection volume: 10 μL.

This quantitative analysis method is accurate and reliable. The sample recovery rate of the detected fat-soluble vitamins and carotenoids is 87.0% to 112.5%, and the minimum detection limit is 0.005 ug/mL to 0.025 ug/mL. As detected by the experiment, the contents of vitamin A, 25-hydroxyvitamin D$_3$, α-tocopherol, γ-tocopherol, lutein, zeaxanthin, β-cryptoxanthin, α-carotene, β-carotene and lycopene in the serum of 20 normal people are 3.05±0.93 μmol/L, 0.081±0.026 μmol/L, 54.2±6.5 μmol/L, 5.69±3.13 μmol/L, 0.23±0.14 μmol/L, 0.055±0.024 μmol/L, 0.19±0.04 μmol/L, 0.062±0.043 μmol/L, 0.72±0.32 μmol/L, and 0.29±0.06 μmol/L, respectively, which are consistent with the content ranges of these nutrients in a normal person reported in references.

Example 11

A method for simultaneously determining fat-soluble vitamins and carotenoids in serum included the following steps:

1) 5 uL of a solution of retinyl acetate and trans-β-apo-8'-carotenal in methanol with a known concentration was added to 250 uL of serum, and the resulting mixture was well mixed;

2) then 100 uL of a solution of N-dodecylpyridinium tetrafluoroborate ([C12Py][BF$_4$]) in n-hexane with a mole fraction of 20% was added to the serum, the resulting mixture was vortexed for 2 min and then centrifuged in a 4° C. centrifuge at 12,000 r/min for 10 min, and the L extract phase was collected;

3) a certain volume of each of stock solutions for fat-soluble vitamin and carotenoid standards was taken and then diluted with simulated serum to give standard solutions with a series of concentrations, and 250 uL of each of the standard solutions was taken and treated according to steps 1) and 2) to give the L extract phases of the standards; and 4) the serum extract phase and the standard extract phases were analyzed by LC, the internal standard method was adopted to establish standard curves for fat-soluble vitamins and carotenoids, and the peak area ratio of each to-be-tested component in serum to the internal standard was compared with the standard curve to obtain the content of each fat-soluble nutrient in serum.

The HPLC analysis was conducted at the following conditions: chromatographic column: YMC C30; mobile phase A: a methanol aqueous solution with a volume fraction of 95%; mobile phase B: a mixed solution of i-propanol/n-hexane with a volume fraction of 75%; flow rate: 1 mL/min; elution mode: gradient elution (0 min to 20 min, 80% A to 0% A; 20 min to 23 min, 0% A to 0% A; 23 min to 30 min, 0% A to 100% A); multi-wavelength detection (324 nm for vitamin A; 263 nm for vitamin D; 290 nm for vitamin E; 254 nm for vitamin K; and 450 nm for carotenoid); column temperature: 25° C., and injection volume: 10 μL.

This quantitative analysis method is accurate and reliable. The sample recovery rate of the detected fat-soluble vitamins and carotenoids is 93.7% to 106.4%, and the minimum detection limit is 0.005 ug/mL to 0.025 ug/mL. As detected by the experiment, the contents of vitamin A, 25-hydroxyvitamin D$_3$, α-tocopherol, γ-tocopherol, lutein, zeaxanthin, β-cryptoxanthin, α-carotene, β-carotene and lycopene in the serum of 30 normal people are 3.18±0.23 μmol/L, 0.087±0.034 μmol/L, 43.2±15.2 μmol/L, 8.14±1.90 μmol/L, 0.38±0.26 μmol/L, 0.065±0.029 μmol/L, 0.21±0.05 μmol/L, 0.071±0.037 μmol/L, 0.83±0.23 μmol/L, and 0.29±0.07 μmol/L, respectively, which are consistent with the content ranges of these nutrients in a normal person reported in references.

The above contents are merely used to illustrate the technical ideas of the disclosure, rather than to limit the protection scope of the disclosure. Any variations made based on the technical solutions according to the technical ideas proposed by the disclosure shall fall within the protection scope as defined by the claims of the disclosure.

What is claimed is:

1. A method for simultaneously determining fat-soluble vitamins and carotenoids in serum, comprising: with an ionic liquid (IL) or a binary mixed solvent composed of an IL and an organic solvent as an extractant, pretreating serum by liquid-liquid extraction (LLE); and with retinyl acetate and trans-β-apo-8'-carotenal as internal standards for fat-soluble vitamins and carotenoids, respectively, subjecting the obtained IL extract phase to high-performance liquid chromatography (HPLC) to determine the contents of fat-soluble vitamins and carotenoids in serum.

2. The method for simultaneously determining fat-soluble vitamins and carotenoids in serum according to claim 1, wherein, the IL is composed of two parts: cation $M^+$ and anion $N^-$; the cation $M^+$ is one of imidazole, pyridine, piperidine, pyrrolidine, amine and phosphoric acid cations with one or more substituents, and the substituent is alkyl, alkenyl or aryl; and the anion $N^-$ is one of hydrophobic anions such as tetrafluoroborate, hexafluoroborate and bis(trifluoromethanesulfonyl)imide.

3. The method for simultaneously determining fat-soluble vitamins and carotenoids in serum according to claim 1, wherein, the IL has a mole percent of 1% to 90% in the binary mixed solvent.

4. The method for simultaneously determining fat-soluble vitamins and carotenoids in serum according to claim 1, wherein, the organic solvent is dichloromethane (DCM), chloroform, dichloroethane, ethyl acetate, n-butanol, n-heptanol, n-octanol, n-pentane, n-hexane, n-heptane, n-octane, cyclopentane, cyclohexane, petroleum ether with a boiling range of 60° C. to 90° C., petroleum ether with a boiling range of 90° C. to 120° C., or toluene.

5. The method for simultaneously determining fat-soluble vitamins and carotenoids in serum according to claim 1, wherein, the serum is pretreated by LLE, with 50 μL to 500 μL of extractant for 250 μL of serum.

6. The method for simultaneously determining fat-soluble vitamins and carotenoids in serum according to claim 1, wherein, the LLE recovery rate for fat-soluble vitamins and carotenoids is 50% to 95%.

7. The method for simultaneously determining fat-soluble vitamins and carotenoids in serum according to claim 1, wherein, the HPLC analysis is conducted at the following conditions:

stationary phase: YMC C30 chromatographic column, 4.6 mm×250 mm, 5 μm;

mobile phase A: a methanol aqueous solution with a volume fraction of more than 90%;

mobile phase B: a mixed solution of i-propanol/n-hexane with a volume fraction of more than 30%;

elution mode: gradient elution, with a flow rate of 1 mL/min;

detection wavelength:

324 nm for vitamin A;

263 nm for vitamin D;

290 nm for tocopherol;

254 nm for vitamin K;

450 nm for carotenoid;

column temperature: 25° C., and injection volume: 10 μL.

* * * * *